United States Patent [19]

Salvo

[11] Patent Number: 4,735,571
[45] Date of Patent: Apr. 5, 1988

[54] DENTAL SPLINT

[76] Inventor: Christopher A. Salvo, 656 King St., Port Chester, N.Y. 10573

[21] Appl. No.: 800,782

[22] Filed: Nov. 22, 1985

[51] Int. Cl.$^4$ ............................................. A61C 5/00
[52] U.S. Cl. ..................................... 433/215; 433/180
[58] Field of Search ................ 433/215, 180, 181, 182

[56] References Cited

U.S. PATENT DOCUMENTS

| | | | |
|---|---|---|---|
| 3,487,545 | 1/1970 | Weissman | 433/215 |
| 4,360,342 | 11/1982 | Salvo | 433/180 |
| 4,380,435 | 4/1983 | Raeder et al. | 433/180 |
| 4,431,417 | 2/1984 | Weissman | 433/182 |
| 4,433,960 | 2/1984 | Garito et al. | 433/215 |

Primary Examiner—John J. Wilson
Attorney, Agent, or Firm—Lowe, Price, LeBlanc, Becker & Shur

[57] ABSTRACT

A dental splint for securing one or more loose, mobile teeth to one or more healthy abutment teeth is provided. The splint utilizes a dental preparation in the lingual or occlusal surface of the teeth and a bar. The preparation should conform to the cross-sectional configuration of the bar with a flat floor, and walls perpendicular thereto. The bar is then chemically bonded to the tooth structure, and a composite covers the bar which is also chemically bonded both to the tooth structure and to the bar. The splint, then, is a unitary structure.

20 Claims, 1 Drawing Sheet

U.S. Patent  Apr. 5, 1988  4,735,571
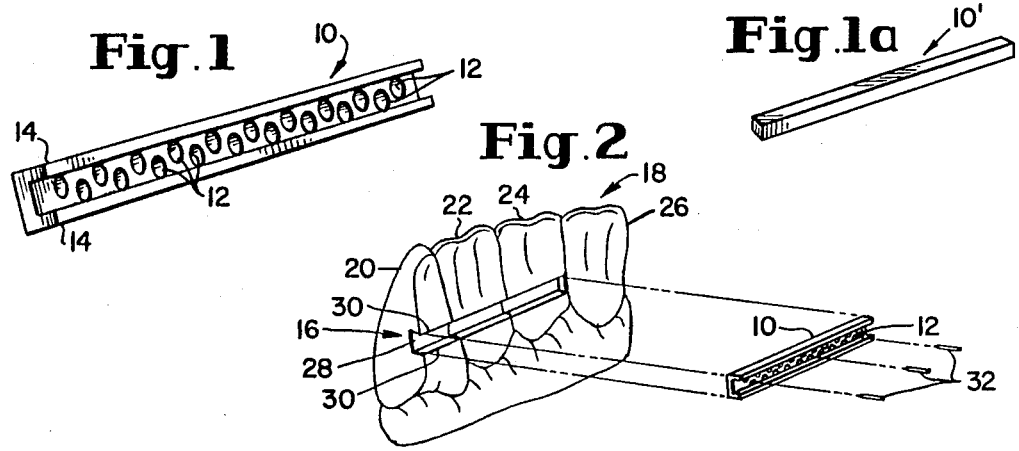
Fig.1
Fig.1a
Fig.2
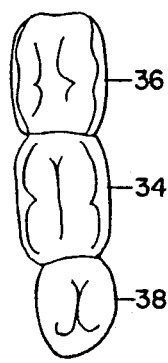
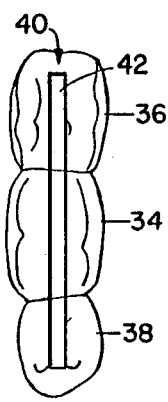
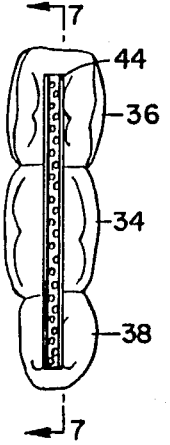
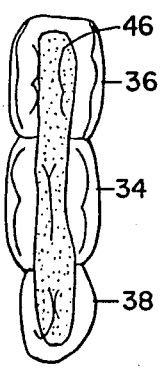
Fig.3  Fig.4  Fig.5  Fig.6
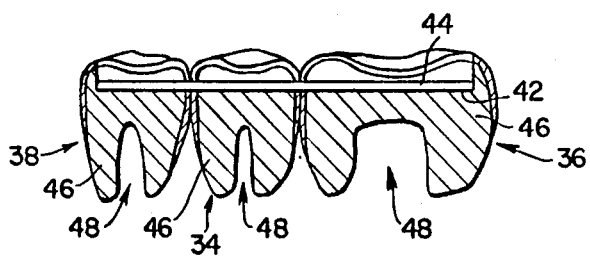
Fig.7

DENTAL SPLINT

This invention relates to a dental splint for permanently supporting loose teeth without extensive excavation or removal of tooth material. The splint of this invention includes a rigid bar retained intracoronally by a chemical bond in a dental preparation with covering composite material also bonded to both the bar and the tooth material. The bonded intracoronal retention then provides a superior, permanent splint without damaging the pulp chamber or pulp material of the teeth involved.

It is known to use a variety of metal materials to provide a splint to support a tooth which has lost its resistance to mobility in the jaw by connecting it to an adjacent healthy tooth. In U.S. Pat. No. 3,822,472, adjacent cavities are drilled in the two teeth, a metal bar is placed in the cavity, and then the cavities are filled either with an amalgam or a filled resin composite. The cavity, however, is not a dental preparation but rather an extensive excavation. More importantly, however, the strength of the splint depends not on the metal bar, but on the amalgam or composite material because only a mechanical bond exists between the bar and the tooth filling material. Large apertures are described in the bar which are filled with the filling material to increase the gripping action, and different shaped bars are described to increase the mechanical gripping action.

In my prior U.S. Pat. No. 4,360,342, there is described a procedure for providing a dental bridge without massive restoration or removal of significant portions of abutment teeth. In that invention, a bar, mesh, or other similar support is provided with a pontic retained thereon. A dental preparation is provided in one or more abutment teeth to receive one or both ends of the support. The support may then be secured to the abutment teeth with tiny screws, pins, or the like and covered with filling material. By using the pins, an extensive removal of portions of abutment teeth is not necessary. The use of pins, screws, or the like to support a superstructure of gold foil, silver restoration material, or self-curing resin or the like is well known. See U.S. Pat. No. 3,434,209, for example. In such cases, channels are drilled into the dentin and screws or pins inserted. The superstructure is then built up on the tooth with the heads of the pins or screws embedded therein. By using nonparallel channels, the mechanical gripping action can be improved.

It has been discovered, however, that a superior splint can be provided either with or without pins as desired by providing a chemically bonded intracoronal retention of the splint. The strength of the splint, then, does not depend upon the composite, amalgam or the like used to cover the splint but rather upon the combination of a bar bonded both to the tooth and to the composite covering.

In the preferred version of this invention, a metal bar preferably of chrome-cobalt alloy is provided. The bar may be approximately 2 millimeters by 1 millimeter by up to about 50 millimeters long. A dental preparation is formed in either the occlusal or lingual surfaces of the loose tooth or teeth and one or more abutment teeth. The preparation should be only slightly larger than the bar itself so that stress on the tooth is avoided. The preparation, however, should not be sufficiently large so that the bar is loose or can rotate in the preparation. The floor should be flat and the walls perpendicular to the pulpal floor. If decay is present, excavation and suitable treatment should be instituted. Decay must be minimal, however, because there must be full basal support, and the bar, as noted above, must fit snugly in the preparation.

Suitable bonding agents are commercially available. For example, Kerr Division of the Sybron Corporation of Romulus, Mich., markets a bonding agent under the trademark Bondlite. Minnesota Mining and Manufacturing Company of St. Paul, Minn., also markets Skotchbond, and Den-mat, Inc. of Santa Maria, Calif., markets an acceptable bonding agent under the trademark Silux. Initially, the bonding agent preferably is used to coat the floors and wall of the preparation and the bar is coated on all sides. A light curing apparatus may be used to cure all surfaces of the bar. The floor of the preparation is then coated with a thin layer of post-exposure curable composite such as that marketed by Den-mat. The bar is then placed firmly on the floor of the preparation.

If pins are to be inserted, all surfaces of the pins or screws should be coated with the bonding agent and the light curing apparatus used with maximum exposure for total curing after placement. Channels, therefore, should be drilled to avoid the pulpal chamber as is well known and the pins inserted through holes provided in the bar. In an embodiment of this invention, a plurality of holes are provided. The holes are interspersed the length of the bar for maximum flexibility in placement of pins or screws. The holes preferably have a diameter of about 0.030"±0.010". In addition, the bar may form a central longitudinal channel along the length thereof so that after the pins are in place, the ends may be bent into the channel.

The bar and pins or screws are then covered with an opaque composite and then a more fully filled composite. The splint may then be finished in a conventional fashion.

The bonding agent then bonds the composite to the dentin and enamel of the tooth and the bar to the same. The chemical bond then insures that the strength of the splint will not be based solely upon the strength of the composite itself but rather upon the entire bonded structure. In this fashion, only minimal removal of enamel to the enamel-dentin juncture or beyond is required. In the absence of caries, extensive excavation of tooth structure is not required and in fact would be entirely avoided.

While the preferred bar of this invention is a chrome-cobalt alloy, any material may be used to construct the bar which is of equivalent rigidity, such as stainless steel, or even a resin. Furthermore, the bar may be coated with composite, thinly, before being used.

As noted above, commercially available bonding agents and composite materials are used herein. The composite normally is a filled acrylic resin, but any commercially available material can be used. Both a composite and bonding agent are described, for example, in U.S. Pat. No. 4,256,603. The bonding agent preferred in that patent is a mixture of silanes in a solvent such as butanol. The solvent also functions as a water displacement agent.

Accordingly, it is an object of this invention to provide an improved splint for loose teeth having superior support without extensive excavation of the tooth structure.

It is another object of this invention to provide a method for splinting loose teeth without excavating cavities therein wherein a dental preparation is used of minimal cross section and depth.

It is another object of this invention to provide a splint for loose teeth consisting of a metal bar which is chemically bonded to the tooth structure and to the covering composite material.

It is yet another object of this invention to provide a splint for loose teeth consisting of a metal or non-metal bar which is chemically bonded both to the tooth structure and to the covering composite material and which may be further supported by a plurality of pins or screws extending through the bar and into the dentin of both the loose and abutment teeth.

These and other objects will become readily apparent with reference to the drawings and following description wherein:

FIG. 1 is a perspective view of an embodiment of the bar of this invention.

FIG. 1a is a perspective view of an alternative embodiment of the bar of this invention.

FIG. 2 is a fragmentary exploded view illustrating the bar of FIG. 1 with pins and a dental preparation in the lingual surfaces of teeth to be splinted.

FIG. 3 is a top view of the occlusal surfaces of teeth to be splinted.

FIG. 4 is a view similar to FIG. 3 including a bar-receiving dental preparation.

FIG. 5 is a view similar to FIG. 4 illustrating the placement of the bar of FIG. 1 in a dental preparation.

FIG. 6 is a top view similar to FIGS. 3-5 illustrating the completed dental splint prior to finishing.

FIG. 7 is a cross-sectional view taken along Line 7—7 of FIG. 5.

With attention to the drawings and to FIG. 1 in particular, the bar 10 of this embodiment defines a U-shaped channel with a plurality of staggered apertures 12 extending therethrough. The apertures 12 preferably are disposed along the entire length of the bar, and are placed between the upstanding legs 14 of the U. Each aperture 12 is preferably of a diameter sufficiently large to accept commercially available dental pins or screws. A diameter of about 0.030"±0.010" is acceptable. In addition, the apertures 12 may be mutually spaced about ½ millimeter apart and staggered as shown in FIG. 1. Less than the number of apertures shown in FIG. 1 may be used if desired.

In the embodiment of FIG. 1a, the bar 10' consists merely of an elongated piece of metal or resin having a substantially rectangular cross section without channel shape, and without apertures.

FIG. 2 illustrates the placement of the bar 10 in a dental preparation 16 in the lingual surfaces of a plurality of teeth 18. In this embodiment, tooth 20 constitutes a healthy abutment tooth. Teeth 22 and 24 may be loose teeth, or tooth 24 may also be a healthy tooth. The bar 10, then, may be used to splint a single loose tooth to a healthy abutment tooth or to abutment teeth on either side which are healthy, or two loose teeth may be splinted to a single healthy tooth. As will also be obvious to those skilled in the art, tooth 26 may be a healthy tooth and dental preparation 16 may be extended to tooth 26 if desired. The dental preparation 16 conforms to the cross-sectional configuration of bar 10 so that when bar 10 is inserted thereinto, it will not be loose. Preparation 16 consists, then, of a flat pulpal floor 28 with walls 30 disposed perpendicular to floor 28. In this embodiment, optional dental pins 32 are shown adapted to extend through apertures 12 into precut channels (not shown) in teeth 18. As will be obvious to those skilled in the art, the channels are disposed in the pulpal floor 28 of preparation 16 and extend into the dentin of the teeth to avoid the pulp chamber.

Pins 32 are optional, and either bar 10 or 10' can be used if desired.

With attention to FIGS. 3-7, there is illustrated the splint of this invention being used to splint a loose tooth 34 to abutment teeth 36 and 38. As has been described relative to the embodiment of FIG. 2, either tooth 36 or 38 could be loose also with the healthy tooth being the abutment tooth for the splint of this invention. In addition, while this embodiment is described relative to two abutment teeth, tooth 34 could be splinted to either tooth 36 or 38.

As shown in FIG. 4, a dental preparation 40 having a flat pulpal floor 42 is prepared in the teeth using conventional methods of dental procedure. It is necessary that the preparation 40 conform to the cross-sectional configuration of bar 44 which is bonded therein to splint the teeth. In order to do so, the walls of the preparation are perpendicular to the floor 42.

Bar 44 is then bonded in the dental preparation 40 and the preparation covered with a composite 46 in the conventional fashion. Subsequently, the outer surface is finished according to conventional procedures.

As shown in FIG. 7, it is important that the dental preparation 40 extend only into the dentin 46 and not into the pulp chamber 48. Bar 44 is intended to be placed into the solid tooth structure.

The procedure for a preferred method for splinting according to this invention is as follows:

The operator should isolate the area into which he wishes to place the splint bar. A rubber dam may be used and is suggested wherever possible. The preparation 40 is made on either the lingual or, as shown in FIGS. 3-7, occlusal surface. The enamel is then etched according to the regular procedures, washed off, neutralized with bicarbonate of soda and cleansed with a 3% peroxide solution across the entire preparation, walls and floor. It is preferred to coat the floor and walls of preparation 40 with an agent having a strong bonding ability to both dentin and enamel. Examples of such agents are, as noted above, BONDLITE, SKOTCHBOND, or SILUX.

Composite material is then placed on the floor of the preparation over the bonding agent. The composite material must have characteristics of total curing to its depths after light application is off because after bar 44 is fitted in the preparation 40, the light will not fully penetrate beneath the bar.

Bar 44 is then preferably cleaned with alcohol and/or 3% hydrogen peroxide. The fitted bar is then coated with the bonding agent on all sides, cured and set aside in a clean area.

The floor 42 of preparation 40 is cleansed with 3% $H_2O_2$, dried, and then coated with a thin layer of post-exposure curable composite such as that manufactured by Den-mat, and the bar is placed snugly in the preparation. The bar 44 is then covered with an opaque composite 46 and then a more fully filled composite. The splint is then finished according to conventional fashion.

If, as in the example of FIG. 2, pins are to be used, the pins may be coated with the bonding agent. The pins are preferably cut to a workable length and inserted into channels previously drilled in the dentin of the teeth through apertures 12 in the bar 10. The ends of the pins are then bent over in the channel provided in bar 10.

Upon completion of the procedure of this invention, a rigid unitary splint will be formed wherein the bar is bonded both to the tooth structure and the composite, and the composite is also bonded both to the tooth structure, dentin and enamel and to the bar. The splint, then, depends for strength on the bonded unitary mass, and not on a composite mechanically gripping the bar and tooth structure.

The invention may be embodied in other specific forms without departing from the spirit or essential characteristics thereof. The present embodiments are therefore to be considered in all respects as illustrative and not restrictive, the scope of the invention being indicated by the appended claims rather than by the foregoing description, and all changes which come within the meaning and range of equivalency of the claims are therefore intended to be embraced therein.

What is claimed is:

1. A method for providing a bonded intracoronal splint for supporting at least one mobile tooth with at least one abutment tooth comprising the steps of:
   providing a substantially rigid bar member having a chemically reactive bondable surface;
   forming a dental preparation in the surfaces of said teeth substantially conforming in cross-sectional configuration to said bar and extending only into the dentin of said teeth, said preparation having a flat floor and walls perpendicular thereto;
   providing a filled resin composite material and a bonding agent for bonding said bar, composite and tooth material;
   coating the walls and floor and said bar with said bonding agent;
   coating the floor of said preparation with said composite;
   mounting said bar in said preparation on said composite coating; and
   covering said bar with said composite so that said composite, bar and teeth will be chemically bonded to form a unitary structure.

2. The method of claim 1 wherein said bar has a plurality of variably interspersed pin or screw receiving apertures therethrough, each aperture having a diameter of about 0.030±0.010 inches.

3. The method of claim 2 wherein said bar forms an outwardly opening, longitudinally extending channel with the apertures located between the outwardly extending flanges thereof.

4. The method of claim 2 further comprising:
   providing a plurality of screws or pins, each coated with said bonding agent; and
   securing said pins or screws, each through an aperture into the dentin of said teeth before covering said bar with said composite material so that said pins or screws will be bonded to the teeth and bar.

5. The method of claim 2 wherein the apertures are mutually spaced about ½ millimeter apart along the length of said bar.

6. The method of claim 2 wherein the apertures are interspersed in non-contiguous groups along the bar length.

7. The method of claim 1 wherein said bar is non-metallic.

8. The method of claim 1 wherein said bar is metallic and has no apertures said bar forming an outwardly opening longitudinally extending channel.

9. The method of claim 1 wherein said bar is non-metallic said bar forming an outwardly opening longitudinally extending channel.

10. The method of claim 1 wherein the preparation is formed on the occlusal surfaces of said teeth.

11. The method of claim 1 wherein the preparation is formed on the lingual surfaces of said teeth.

12. A method for providing a bonded intracoronal splint for supporting at least one mobile tooth with at least one abutment tooth comprising the steps of:
   providing a substantially rigid bar member having a roughened bondable surface;
   forming a dental preparation in the surfaces of said teeth substantially conforming in cross-sectional configuration to said bar and extending only into the dentin of said teeth, said preparation having a flat floor and walls perpendicular thereto;
   providing a filled resin composite material and a bonding agent for bonding said bar, composite and tooth material;
   coating the walls and floor and said bar with said bonding agent;
   coating the floor of said preparation with said composite;
   mounting said bar in said preparation on said composite coating; and
   covering said bar with said composite so that said composite, bar and teeth will be chemically bonded to form a unitary structure.

13. The method of claim 12 wherein said bar has a plurality of variably interspersed pin or screw receiving apertures therethrough, each aperture having a diameter of about 0.030 plus or minus 0.010 inches.

14. The method of claim 13 wherein said bar forms an outwardly opening, longitudinally extending channel with the apertures located between the outwardly extending flanges thereof.

15. The method of claim 13 further comprising:
   providing a plurality of screws or pins, each coated with said bodning agents; and
   securing said pins or screws, each through an aperture into the dentin of said teeth before covering said bar with said composite material so that said pins or screws will be bonded to the teeth and the bar.

16. The method of claim 13 wherein the apertures are mutually spaced about one half millimeter apart along the length of said bar.

17. The method of claim 13 wherein the apertures are interspersed in non-contiguous groups along the bar length.

18. The method of claim 12 wherein the bar is non-metallic.

19. The method of claim 12 wherein the bar is metallic and has no apertures, said bar forming an outwardly opening, longitudinally extending channel.

20. The method of claim 12 wherein the bar is non-metallic and forms an outwardly opening, longitudinally extending channel.

* * * * *